United States Patent [19]
Sellstedt et al.

[11] 4,096,153
[45] Jun. 20, 1978

[54] ARYLENE-BIS-TETRAZOLE-5-CARBOXAMIDES

[75] Inventors: John H. Sellstedt, Pottstown; Dieter H. Klaubert, West Chester, both of Pa.

[73] Assignee: American Home Products Corporation, New York, N.Y.

[21] Appl. No.: 761,501

[22] Filed: Jan. 21, 1977

[51] Int. Cl.$^2$ .......................................... C07D 257/04
[52] U.S. Cl. ................................. 260/308 D; 424/209
[58] Field of Search .................................... 260/308 D

*Primary Examiner*—Donald G. Daus
*Assistant Examiner*—D. B. Springer
*Attorney, Agent, or Firm*—Richard K. Jackson

[57] ABSTRACT

Anti-allergic agents of N,N'-arylene-bis-tetrazole-5-carboxamide derivation, pharmaceutically acceptable salts thereof and N-protected intermediates therefor.

5 Claims, No Drawings

ARYLENE-BIS-TETRAZOLE-5-CARBOXAMIDES

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust, milk and wheat, whether inhaled or ingested. Atopic hypersensitivity is found in man, dog, and other animals. Its occurrance is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after two hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reactions(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines(5-HT) or anti-inflammatories, or (4) stimulate the cell under attack to negate the action of the mediator through the action of bronchodilators such as Isuprel ® or a Xanthine.

A compound typifying anti-allergic activity by blocking reactions(s) within the mast cells, thereby preventing the production and release of mediators, is disodium cromoglycate. (INTAL ®).

DESCRIPTION OF THE INVENTION

In accordance with this invention, there is provided a group of anti-allergic agents of the formula:

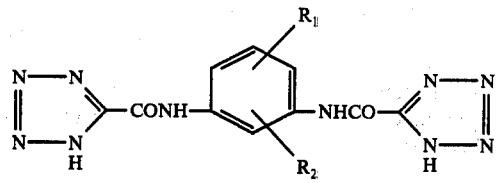

in which $R_1$ and $R_2$ are, independently, hydrogen, cyano, trifluoromethyl, halo, nitro, lower alkanoyl, lower alkoxy or carbamoyl or a pharmaceutically acceptable salt thereof. In addition, this invention provides protected intermediates employed in the production of the arylene-bis-tetrazole-5-carboxamides, which intermediates present the structural formula:

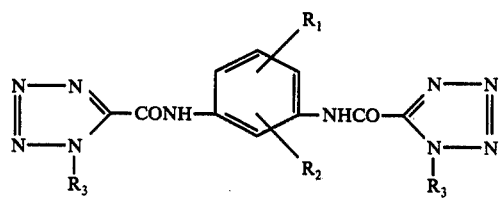

in which $R_1$ and $R_2$ are defined above and the two $R_3$ groups represent any readily removable protective group such as those described by F. Weygand et al., Deut. Ber. Chem. 101, 3623-3641(1968). For example, the protective group may be benzyl, 4-methoxybenzyl, 2,4-dimethoxybenzyl, 2,4,6-trimethoxybenyl and the like.

The pharmaceutically acceptable salts of the arylene-bis-tetrazole-5-carboxmaides of this invention are the alkali metal (e.g. sodium or potassium), the alkaline earth metal (e.g. calcium or magnesium), lower alkyl amine (e.g. ethylamine, i-propylamine, n-propyl amine, etc.) di-lower alkyl amine (e.g. dimethylamine, diethylamine, etc), tri-lower alkylamine (e.g. trimethylamine, triethylamine, tripropylamine, etc.) or a water solubilizing amine such as the omega hydroxy analogues of the primary and secondary lower alkylamines as well as more complex amines such as N,N'-dibenzylethylenediamine.

Throughout this disclosure, the term "lower" used to modify such terms as alkanoyl, alkoxy, alkylamine, etc. is intended to define the carbon atom content of the modified term as from 1 to 6 carbon atoms per hydrocarbon radical. The term "halo" is intended to embrace the chloro, bromo, fluoro and iodo groups. It should also be understood that the tetrazole moieties depicted as 1H-tetrazole-5-carboxamides may appear when unprotected as the 2H-tautomer and it is applicants intent to embrace the 2H-tautomer as the full equivalent of the depicted 1H-tautomer. The tautomers may be depicted as follows:

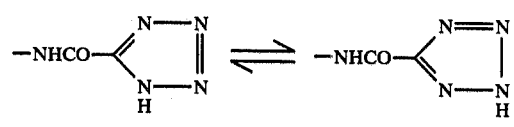

1H      2H

The compounds of this invention are prepared by reaction of an appropriately substituted 1,3-phenylenediamine with two equivalents of 1-protected-1H-tetrazole-5-carbonyl chloride followed by deprotection of the tetrazole moieties and conversion to a desired pharmaceutically acceptable salt where water solubility is desired. Thus,

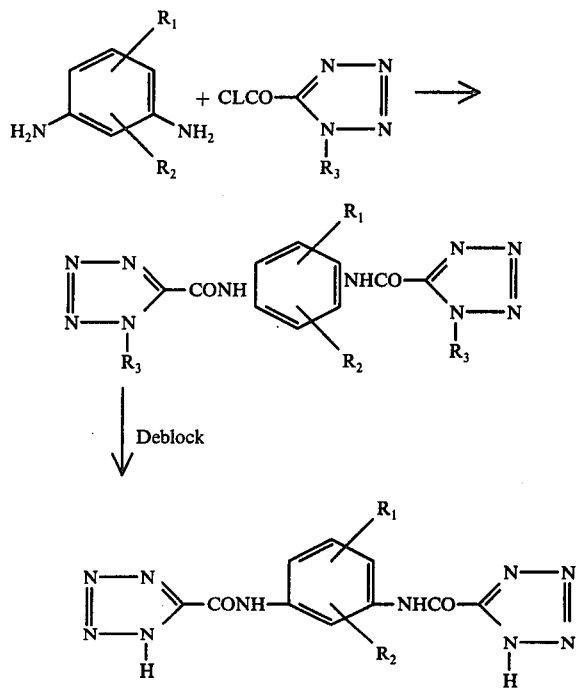

The substituted phenylenediamine reactants are known compounds or may be readily produced by techniques well known to the chemist. The 1-protected-1H-tetrazole-5-carbonyl chloride reactant is prepared by the procedure disclosed in our copending application Ser. No. 669,570 filed Mar. 23, 1976. Deprotection of the tetrazole moieties after condensation with the arylenediamine is performed by methods known in the art.

The anti-allergy compounds of this invention relieve atopic allergic manifestations when administered orally, topically, intraperitoneally, intramuscularly, intravenously and as inhalents.

The technique employed to establish the anti-allergic activity of the bic-1H-tetrazole-5-carboxamide derivatives of this invention is reported in immunology, vol, 16, pp. 749–760 (1969) and involves four male Charles River rats (200-250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Forty-eight hours after the initial injections, the test compound is administered at graded dosage levels by the desired route. Five minutes later one milliliter of a 0.8 percent solution of ovalbumin contains 5 mg. of Evans blue dye is injected intravenously. After forty minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants have found that the compounds of this invention, in a manner believed to be similar to the function of INTAL ®, block reaction(s) in the mast cell leading to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

In other words, the compounds of this invention block the release of mediators commonly resulting from the antigen-antibody reaction as exemplified in a passive cutaneous anaphylaxis test (PCA) using rat homocytotropic antibody - a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same route of administration as INTAL ®.

Thus, there is provided herewith the means for suppressing allergic manifestations of atopic immediate sensitivity in warm-blooded, human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, intraperitoneal, intramuscular or intravenous routes as well as via inhalation. The compounds of this invention may be administered in conjunction with known compounds effecting anti-histaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions, the latter for use as inhalents. When aqueous solutions are desired for administration, the salts of this invention provide ready solubility without solubilizing additives.

The following specifically exemplified compounds demonstrated marked activity when administered intraperitoneally at a dosage of 10 milligrams per kilogram host body weight with effective inhibition evidenced at doses at low as 0.10 milligrams per kilogram. Approximately 100 percent inhibition was evidenced by the product of Example 1 at a dose as low as 0.01 milligrams per kilogram administered intravenously. The effective oral dosage for the product of Example 1 extended from 43 percent inhibition at 1.0 mg/kg to 88 percent inhibition at 10.0 mg/kg and 100 percent inhibition at 100 mg/kg, while the product of Example 2 provided 62 percent inhibition at 50 mg/kg. Thus, the effective dose varies with the route of administration, lying within the range of between 0.1 to 100.0 milligrams per kilogram host body weight. Hence, for practical administration the unit dosage contemplated for human and non-human use based upon the potency of the compound administered lies from about 1.0 milligram to about 1 gram to be administered when necessary and to the degree of the desired response, in single or plural doses under the guidance of a physician.

EXAMPLE 1

N,N'-(5-Cyano-1,3-phenylene)bis[1H-tetrazole-5-carboxamide]Disodium Salt 1-(4-Methoxybenzyl)-1H-tetrazole-5-carbonyl chloride (25.27 g., 0.1 mol.) in 400 ml. of cold methylene chloride is dipped into a solution of 6.65 g. (0.05 mol.) of 3,5-diaminobenzonitrile and 0.3 ml. (.103 mol) of pyridine in 400 ml. of methylene chloride at 0°–5° C. over 10 min. The solution is stirred for 2 hr. at 0°–5° C., 1 hr. at 30° C., and add 500 ml. water. The organic layer is successively washed with water, cold 0.5N HCl, saturated NaHCO$_3$, brine, and is dried with CaCl$_2$. Evaporation of the methylene chloride gives 21 g. (74%) of N,N'-(5-cyano-1,3-phenylene)bis[1-(4-metoxyphenylmethyl)-1H-tetrazole-5-carboxyamide], m.p. 208°–10° C., after crystallization from acetonitrile.

Anal. Calcd. for $C_{27}H_{23}N_{11}O_4$: C, 57.34; H, 4.10; N, 27.25. Found : C, 57.67; H, 4.01; N, 27.56.

The protected tetrazole (18.36 g., 0.032 mol.) and anisole (35.04 g.) are dissolved in 350 ml. of trifluoroacetic acid under nitrogen, and the mixture is refluxed for 30 min. The trifluoroacetic acid is removed on a rotary evaporator at 40° C., and the residue is triturated with diethyl ether. The mixture is filtered and the cake is washed with diethyl ether giving 11.2 g. of N,N'-(5-cyano-1,3-phenylene)bis(1H-tetrazole-5-carboxamide) as a white solid, m.p. 265° C. dec.

The white solid (9.8 g., 0.0301 mol.) is dissolved in 200 ml. of hot absolute ethanol, and 10.21 ml. (0.0601 mol.) of 5.99N sodium hydroxide is added, giving the title compound as a white precipitate, 8.0 g., m.p.>310° C.

Anal. Calcd. for $C_{11}H_5N_{11}Na_2O_2 \cdot 1\frac{1}{2} H_2O$; C, 33.34; H, 2.03; N, 38.89. Found: C, 33.15; H, 2.18; N, 38.95.

EXAMPLE 2

N,N'-(2-Chloro-5-cyano-1,3-phenylene)bis[1H-tetrazole-5-carboxamide]Disodium Salt In a manner similar to example 1, but starting with 2-chloro-5-cyano-1,3-phenylenediamine (5.87 g., 0.035 g., 0.035 mol.), the intermediate N,N'-(2-chloro-5-cyano-1,3-phenylene)bis[1-(4-methoxyphenylmethyl)-1H-tetrazole-5-carboxamide] is prepared (11.60 g., m.p. 223°–225° C. from acetonitrile).

Anal. Calcd. for $C_{27}H_{22}ClN_{11}O_4$: C, 54.05; H, 3.69; N, 25.68. Found: C, 53.05; H, 3.58; N, 25.46.

In a manner similar to example 1, 10.93 g. of the above protected tetrazole is deprotected, converted to the title disodium salt (3.17 g.) and collected as crystals from water, m.p.>300° C.

Anal. Calcd. for $C_{11}H_4ClN_{11}NaO_4 \cdot 0.75H_2O$: C, 31.67; H, 1.33; N, 36.94. Found: C, 31.67; H, 0.87; N, 36.87.

EXAMPLE 3

N,N'-(2-Chloro-5-trifluoromethyl-1,3-phenylene)-bis[1H-tetrazole-5-carboxamide]Disodium Salt In a manner similar to example 1, but starting with 2-chloro-5-trifluoromethyl-1,3-phenylenediamine (10.53 g., 0.05 mol), the intermediate N,N'-(2-chloro-5-trifluoromethyl-1,3-phenylene)-bis[1-(4-methoxyphenylmethyl)-1H-tetrazole-5-carboxamide] is prepared (17.83 g., m.p. 185°–186° C° from acetonitrile).

Anal. Calcd. for $C_{27}H_{22}ClF_3N_2O_4$: C, 50.43; H, 3.45; N, 21.78. Found: C, 49.90; H, 3.20; N, 21.30.

In a manner similar to example 1, 17.56 g. of the above protected tetrazole is deprotected and the title disodium salt (7.53 g., m.p. 295° C° dec.) is freeze-dried from an aqueous solution of the tetrazole free acid (crystallized from ethanol) and two moles of sodium hydroxide.

Anal. Calcd. for $C_{11}H_4ClF_3N_{10}Na_2O_2$: C, 26.72; H, 1.89; N, 28.33. Found: C, 27.12; H, 1.52; N, 27.92.

The products of Examples 1 and 3 exhibit anti-secretory activity when tested in the four hour pylorus ligated rat test according to the procedure of Shay et al., Gastroenterology 26 906–913 (1954) at from about 1 to 25 milligrams per kilogram host body weight and at 25 milligrams per kilogram host body weight, respectively. Therefore, these compounds are also useful an anti-secretory agents for the treatment of peptic ulcer disease.

What is claimed is:

1. A compound of the formula:

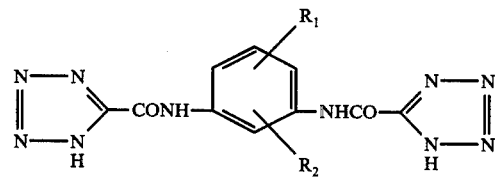

in which
R$_1$ and R$_2$ are , independently, hydrogen, cyano, trifluoromethyl, halo, nitro, lower alkanoyl, lower alkoxy or carbamoyl
or a pharmaceutically acceptable salt thereof.

2. A compound of claim 1 which is N,N'-(5-cyano-1,3-phenylene)bis(1H-tetrazole-5-carboxamide) or a pharmaceutically acceptable salt thereof.

3. A compound of claim 1 which is N,N'-(2-chloro-5-cyano-1,3-phenylene)bis(1H-tetrazole-5-carboxamide) or a pharmaceutically acceptable salt thereof.

4. A compound of claim 1 which is N,N'-(2-chloro-5-trifluoromethyl-1,3-phenylene)bis(1H-tetrazole-5-carboxamide) or a pharmaceutically acceptable salt thereof.

5. A compound of the formula:

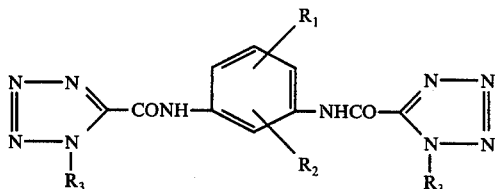

in which
R$_1$ and R$_2$ are, independently, hydrogen, cyano, trifluoromethyl, halo, nitro, lower alkanoyl, lower alkoxy or carbamyl;
and the two R$_3$ groups are protective groups selected from the group consisting of benzyl, 4-methoxybenzyl, 3,4-dimethoxybenzyl and 2,4,6-trimethoxybenzyl.

* * * * *